United States Patent
Konrad et al.

(10) Patent No.: US 7,722,811 B2
(45) Date of Patent: May 25, 2010

(54) TISSUE PROCESSOR

(75) Inventors: Marc Konrad, Dossenheim (DE); Stefan Künkel, Karlsruhe (DE); Holger Metzner, Nussloch (DE); Eberhard Sendobry, Rimbach (DE); Markus Dobusch, Wiesloch-Baiertal (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 788 days.

(21) Appl. No.: 11/562,710

(22) Filed: Nov. 22, 2006

(65) Prior Publication Data

US 2007/0122910 A1  May 31, 2007

(30) Foreign Application Priority Data

Nov. 29, 2005 (DE) .................. 10 2005 057 191

(51) Int. Cl.
G01N 21/00 (2006.01)
(52) U.S. Cl. .................. 422/63; 422/64; 422/65; 422/67; 422/99; 422/100; 422/102; 222/181.1; 222/185.1
(58) Field of Classification Search ............ 422/63–67, 422/99–100, 102; 222/309, 319, 181.1, 185.1
See application file for complete search history.

(56) References Cited

U.S. PATENT DOCUMENTS

| 3,771,490 | A | * | 11/1973 | Kinney et al. ............ 118/698 |
| 4,810,659 | A | * | 3/1989 | Higo et al. ................ 436/180 |
| 5,683,658 | A | | 11/1997 | Reischl et al. |
| 2005/0124028 | A1 | | 6/2005 | Windeyer et al. |

FOREIGN PATENT DOCUMENTS

| GB | 2319608 A | 5/1998 |
| JP | 5745350 A | 3/1982 |

OTHER PUBLICATIONS

Leica Microsystems Nussloch GmbH, Nussloch, Germany: brochure entitled "Leica ASP 300—The Advanced Smart Tissue Processor"; at least as early as Apr. 30, 2001.

* cited by examiner

*Primary Examiner*—Jyoti Nagpaul
(74) *Attorney, Agent, or Firm*—Hodgson Russ LLP

(57) ABSTRACT

A tissue processor (1) is described, having a retort (2) for processing histological samples with different reagents, having multiple reagent reservoir vessels (3), and having a conduit system and a control device (5) for delivering reagents out of the reagent reservoir vessels (3) into the retort (2). A suction conduit (11) projects into each reagent reservoir vessel (3) through the vessel opening (7) for reagent withdrawal. A closure system (12) having an externally tapered and internally hollow closure plug (13) is provided for closing off the vessel opening (7). The suction conduit (11) is guided through a cavity (14) of the closure plug (13) for reagent withdrawal.

4 Claims, 3 Drawing Sheets

TISSUE PROCESSOR

CROSS REFERENCE TO RELATED APPLICATIONS

This application claims priority of German patent application no. 10 2005 057 191.3 filed Nov. 29, 2005, which is incorporated by reference herein.

FIELD OF THE INVENTION

The present invention relates to a tissue processor of a type comprising a retort for processing histological samples with different reagents, the tissue processor including multiple reagent reservoir vessels that each have at least one vessel opening, a conduit system and a control device for delivering reagents out of the reagent reservoir vessels into the retort, and a suction conduit projecting into each reagent reservoir vessel through the vessel opening for reagent withdrawal.

BACKGROUND OF THE INVENTION

Tissue processors are used for automatic processing of histological samples for subsequent section preparation with a microtome, followed by microscopic examination. The tissue of the sample must firstly, in multiple stages, be dewatered, purified, hardened, and then stabilized with paraffin. This is accomplished with various reagents to which the sample is exposed.

A tissue processor that permits large automatic processing of the samples is depicted and described in the Leica document "Leica ASP 300," Leica Microsystems Nussloch GmbH, order no. 0704-2-1-103, April 2001.

The tissue processor comprises a retort as a processing station for the samples. The retort is connected via a tubing or piping system to multiple standardized reagent reservoir vessels for the different reagents. By way of a pump system and an electronic control system, the respective reagents can be automatically pumped from the reservoir vessels into the retort and back.

The reagent reservoir vessels arranged in the tissue processor must from time to time be emptied and replaced with unused reagents. The tissue processor comprises for that purpose a connector for an external tubing system through which each individual reagent reservoir vessel can be emptied and refilled. This procedure of course requires a plurality of external vessels that must be stored separately in the laboratory. There also exists a risk of confusion in the context of vessels having fresh and used reagents.

Simple and direct exchange of the reagent reservoir vessels is also thwarted by the different dimensions of the external refill reagent vessels.

SUMMARY OF THE INVENTION

It is therefore an object of the present invention to make possible direct changing of differently dimensioned reagent reservoir vessels.

This object is achieved, according to the present invention, by the features described in the present specification. Further advantageous embodiments of the invention are the subject matter of the dependent claims.

The invention is notable for the fact that a closure system having an externally tapered and internally hollow closure plug is provided for closing off the vessel opening. The suction conduit is guided through the cavity of the closure plug for reagent withdrawal. With the externally tapered closure plug, reagent reservoir vessels having different opening diameters can be connected with no need to provide additional adapters or other modifications on the tissue processor.

In a refinement of the invention, the diameter of the cavity in the closure plug is dimensioned to be larger than the outside diameter of the suction conduit. An annular opening is thereby formed between the two diameters in the closure plug.

In a further embodiment of the invention, the annular opening is connected to a gas conduit, so that the reagent reservoir vessel can be aerated and vented through the gas conduit and therefore no harmful vapors can emerge.

In a refinement of the invention, the closure plug is mounted or embodied resiliently, so that a secure frictional connection is created between the reagent reservoir vessel and the closure system.

In a further embodiment of the invention, the closure plug is joined to a bellows, so that different overall heights can also be compensated for in the context of the reagent reservoir vessels.

In a refinement of the invention, the gas conduit is connected to a filter device so that no harmful vapors can enter the environment upon venting of the reagent reservoir vessels.

BRIEF DESCRIPTION OF THE DRAWINGS

The invention will be explained in more detail with reference to an exemplifying embodiment, with the aid of the schematic drawings in which.

DETAILED DESCRIPTION OF THE INVENTION

Figure 1:
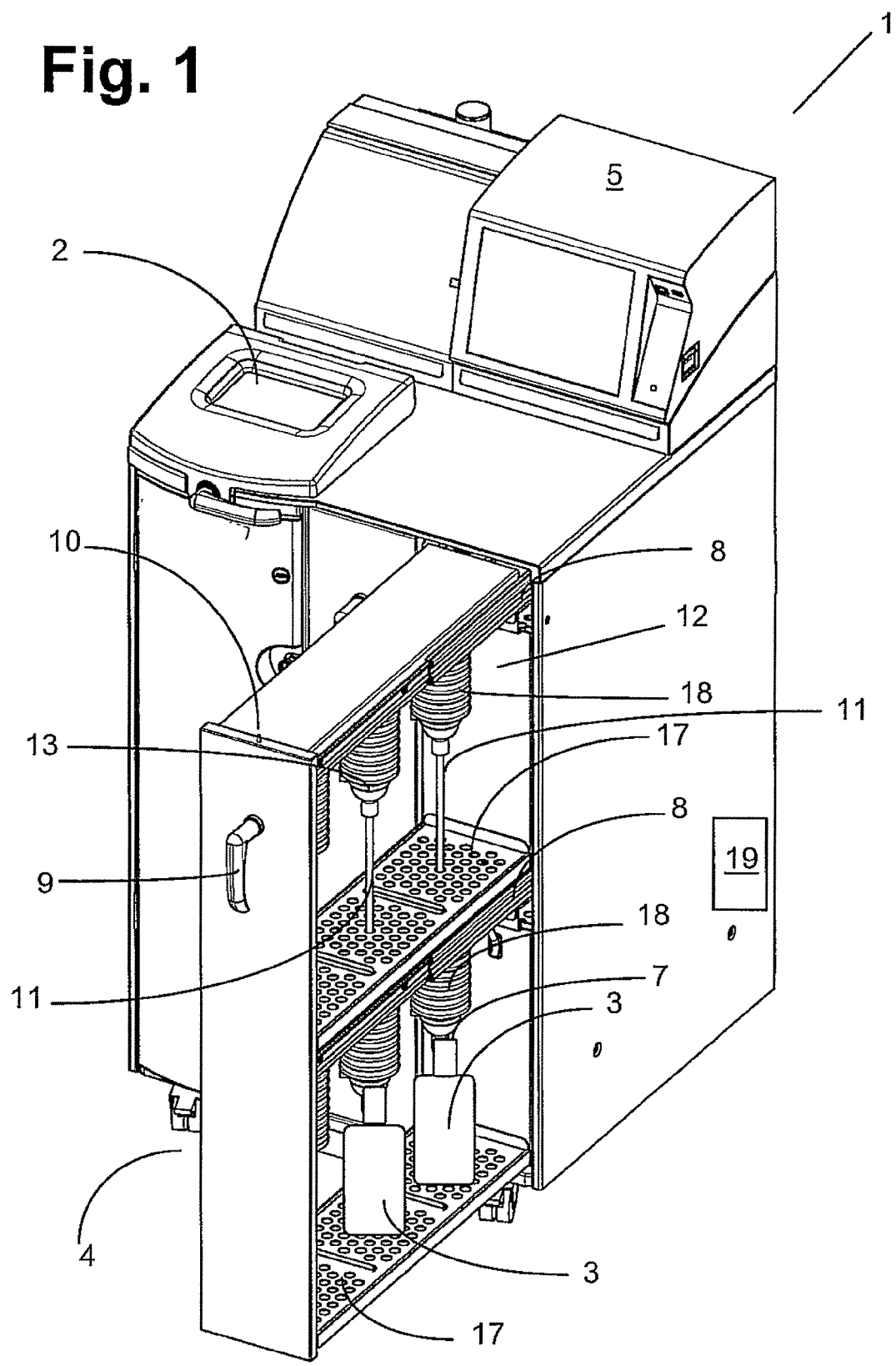
FIG. 1 is a view of the tissue processor with a drawer.

FIG. 1 is a view of a tissue processor 1 having a retort 2 for the processing of samples and having a control device 5 including a pump system (not shown separately). Tissue processor 1 is equipped with a drawer 4 that is joined via telescoping rails 8 to the housing of processor 1. Drawer 4 comprises two plates 17, arranged one above another, as supports for multiple reagent reservoir vessels 3. Reagent reservoir vessels 3 are respectively connected, via a closure system 12, to a conduit system through which the reagents are transported out of reagent reservoir vessels 3 into retort 2 and from there back out again. Also provided is a gas conduit (not depicted here) that is connected to a filter device 19 in tissue processor 1 and filters vapors emerging from reagent reservoir vessels 3.

Closure system 12 comprises an externally tapered closure plug 13 having a suction line 11 that is guided in the interior of closure plug 13 and projects through vessel opening 7 into the interior of reagent reservoir vessel 3. The outside diameter of closure plug 13 may change linearly such that the plug's outer surface is conically shaped, or it may change non-linearly such that the plug's outer surface is curved. Closure plug 13 is joined to a bellows 18 with which different overall heights of reagent reservoir vessels 3 can be compensated for. Preferably, at least an outer portion of the closure plug 13 is formed of a resilient material for snug frictional fit within vessel opening 7.

Arranged on a front side of drawer 4 is a pivotable lever 9 that is mechanically joined to a locking bolt 10 in order to retain drawer 4 in the housing of tissue processor 1. The lever simultaneously serves as a handle for moving drawer 4.

Figure 2:
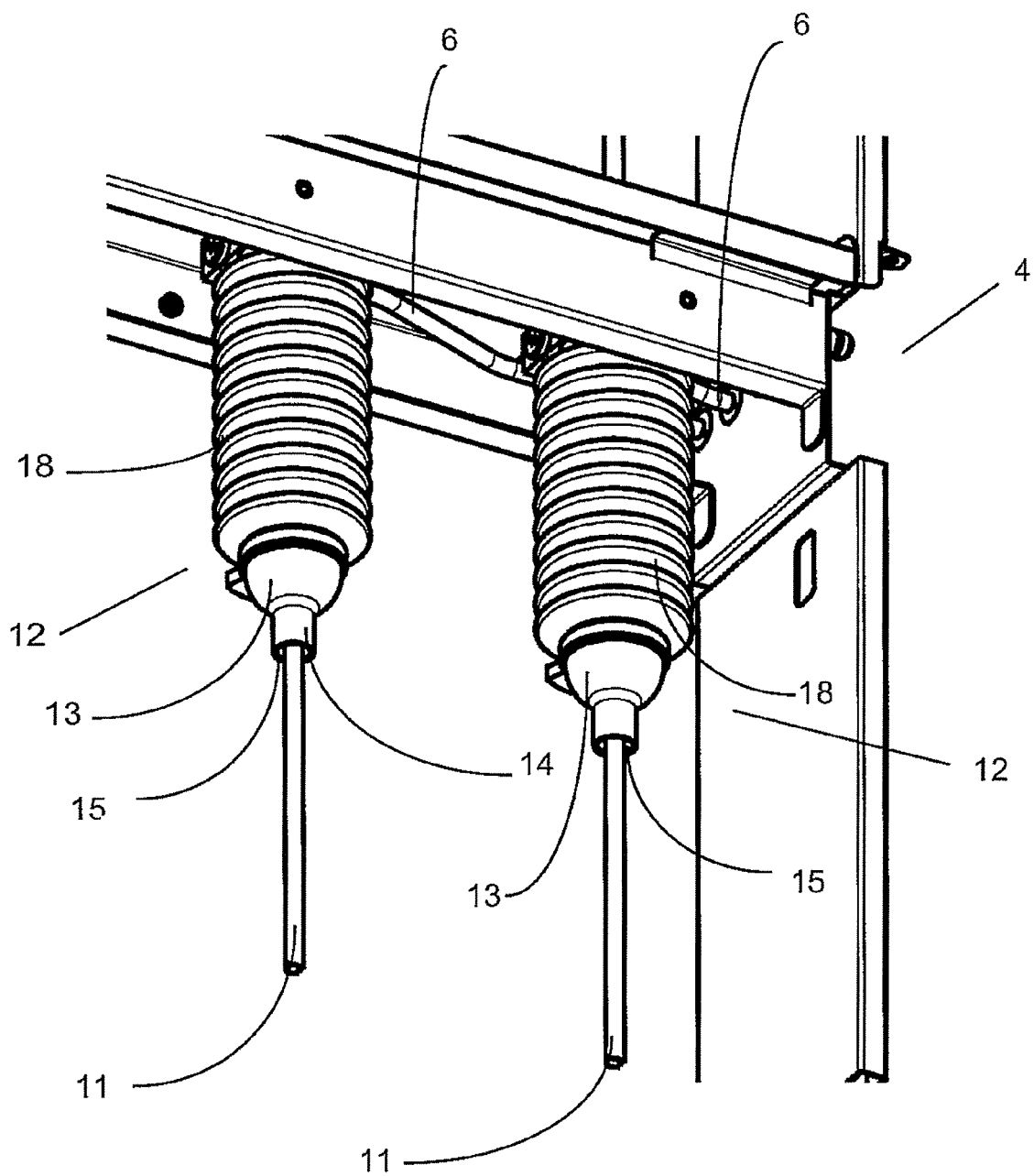
FIG. 2 is a detail view of the closure system.

FIG. 2 is a detail view of closure system 12 with conduit system 6 and the resilient bellows 18. Bellows 18 carries the tapered closure plug 13, which is equipped with a cavity 14. Suction conduit 11, whose outside diameter is dimensioned to be smaller than cavity 14, is guided in that cavity 14. An annular opening 15 is thereby formed in closure plug 13. This annular opening 15 is of cylindrical configuration, and is connected via bellows 18 to a gas conduit (FIG. 3) for aerating and venting the reagent reservoir vessels.

Figure 3:
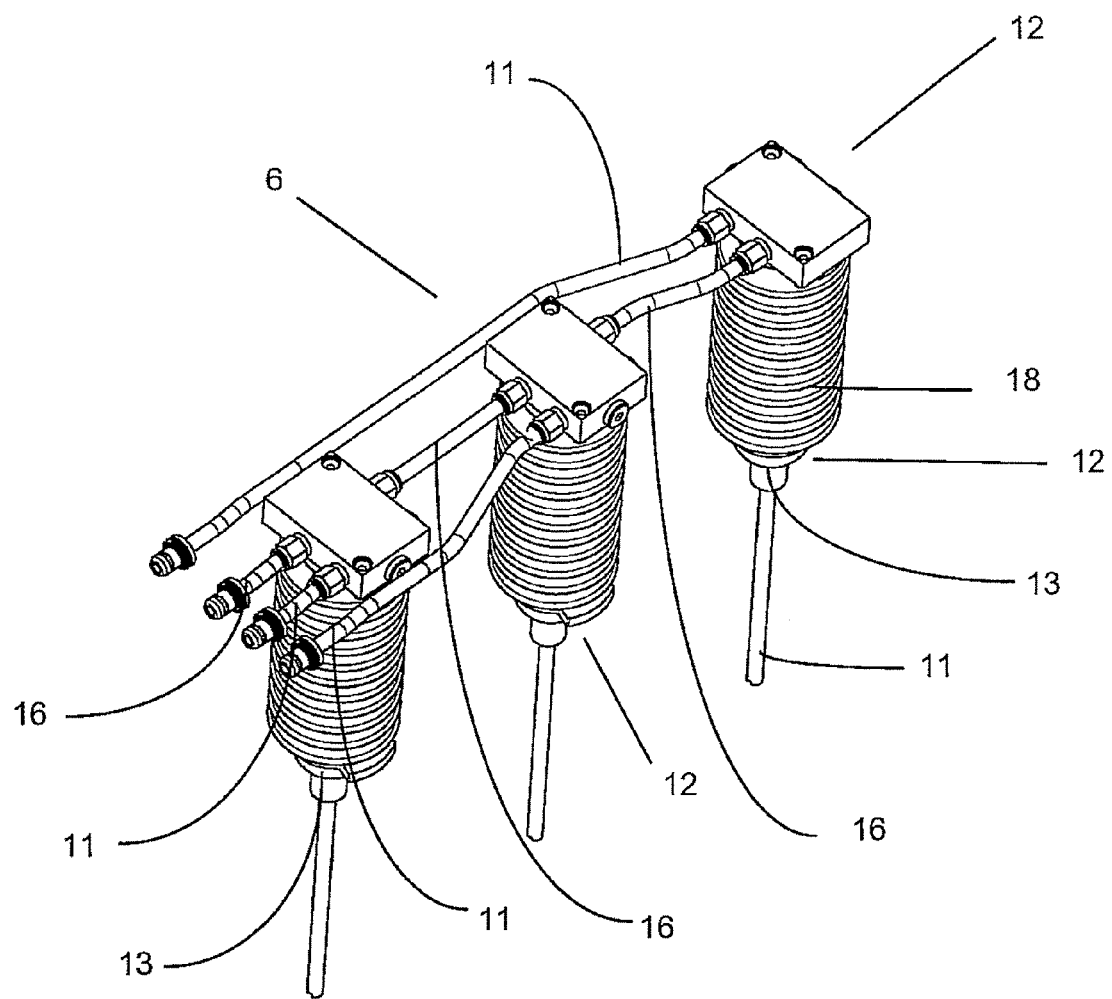
FIG. 3 is a detail view of the closure system with the conduit connections.

FIG. 3 is a detail view of closure system 12 with conduit system 6. Each closure system 12 is equipped with an individual suction conduit 11 and connected to a common gas conduit 16. Gas conduit 16 is connected to filter device 19 (FIG. 1). Through suction conduits 11, the retort is filled with reagents from the reagent reservoir vessels. After sample processing, the reagents are conveyed out of the retort, through suction conduits 11, back into the reagent reservoir vessels. Vapors occurring in this context are delivered through gas conduit 16 to the filter device, or the reagent reservoir vessels are vented via gas conduit 16.

PARTS LIST

1 Tissue processor
2 Retort
3 Reagent reservoir vessel
4 Drawer
5 Control device
6 Conduit system
7 Vessel opening
8 Telescoping rail
9 Lever
10 Locking bolt
11 Suction conduit
12 Closure system
13 Closure plug
14 Cavity of 13
15 Annular opening
16 Gas conduit
17 Plate
18 Bellows
19 Filter device

What is claimed is:

1. A tissue processor comprising:
   a retort for processing histological samples with different reagents;
   a plurality of reagent reservoir vessels each including a vessel opening;
   a conduit system communicating between the plurality of vessels and the retort, the conduit system including a plurality of suction conduits each projecting into a respective one of the plurality of vessels through the vessel opening for reagent withdrawal;
   a closure system for closing the vessel openings, the closure system including a plurality of externally-tapered closure plugs each received by a respective vessel opening, each of the plurality of closure plugs having a cavity extending through the closure plug, wherein the suction conduit associated with the vessel is guided through the cavity of the respective closure plug and the cavity of each of the plurality of closure plugs has an inside diameter greater than an outside diameter of the suction conduit guided therethrough, and an annular opening is defined between the outside diameter and the inside diameter; and
   wherein the closure system further includes a plurality of bellows and each of the plurality of closure plugs is joined to a respective one of the plurality of bellows;
   a control device including a pump system for delivering reagents out of the reagent reservoir vessels and into the retort by way of the conduit system.

2. The tissue processor according to claim 1, further comprising a gas conduit connected to the annular opening associated with each of the plurality of closure plugs.

3. The tissue processor according to claim 2, further comprising a filter device, wherein the gas conduit is connected to the filter device.

4. The tissue processor according to claim 1, wherein at least an outer portion of the closure plug is formed of a resilient material.

\* \* \* \* \*